Figure 1:
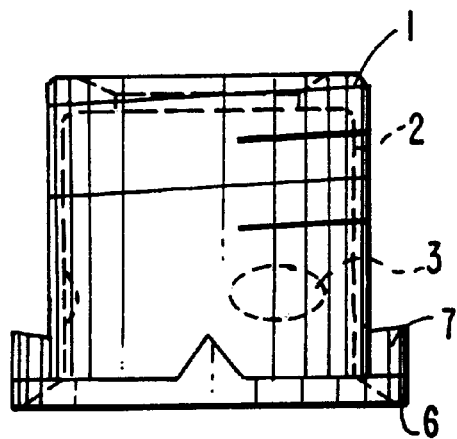

United States Patent

Hansen et al.

Patent Number: 6,126,646
Date of Patent: *Oct. 3, 2000

[54] ADAPTOR TOP

[75] Inventors: Ib Hansen, Herlev; Søren Mikkelsen, Holte; Frits Frydendal Bonnichsen, Lynge, all of Denmark

[73] Assignee: Novo Nordisk A/S, Bagsværd, Denmark

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/901,872

[22] Filed: Jul. 29, 1997

Related U.S. Application Data

[63] Continuation of application No. 08/313,651, Sep. 26, 1994, Pat. No. 5,693,027, which is a continuation of application No. 08/053,502, Apr. 27, 1993, abandoned, which is a continuation of application No. 07/768,684, Oct. 9, 1991.

[30] Foreign Application Priority Data

Sep. 21, 1990 [DK] Denmark .................................. 2282/90
May 16, 1991 [DK] Denmark .................................... 926/91

[51] Int. Cl.[7] .................................................. A61M 5/00
[52] U.S. Cl. ............................................ 604/256; 604/232
[58] Field of Search ..................................... 604/201, 256, 604/81, 87, 403, 415, 416, 905, 207, 208, 209, 210, 232, 414, 243, 240; 215/249, 296, 256

[56] References Cited

U.S. PATENT DOCUMENTS

| 3,375,825 | 4/1968 | Keller ................................... 604/201 X |
| 4,619,651 | 10/1986 | Kopfer et al. ........................... 604/415 |
| 4,664,656 | 5/1987 | Taddei ..................................... 604/241 |
| 4,768,568 | 9/1988 | Fournier et al. ..................... 604/415 X |
| 5,269,317 | 12/1993 | Bennett ............................... 604/403 X |
| 5,498,253 | 3/1996 | Bonnichsen ......................... 604/415 X |

*Primary Examiner*—Wynn Wood Coggins
*Assistant Examiner*—A. T. Nguyen
*Attorney, Agent, or Firm*—Steve T. Zelson, Esq.

[57] ABSTRACT

A plastic adaptor top for adapting to a chosen syringe a standard cartridge of the kind having a neck with a flange and being closed by a rubber membrane sealingly secured against the flange by a metal cover having its edge beaded behind the flange. This plastic top has a bore for receiving the neck part of the cartridge, which bore has a diameter making it fit over the metal cover and is provided with protrusions gripping behind the edge of the metal cover when the neck part is inserted in the bore. The outer contour of the adaptor top is provided with threads coaxial with the bore to receive a needle hub in a way causing the needle to penetrate the membrane of the cartridge when the hub is mounted on the thread of the plastic top.

5 Claims, 2 Drawing Sheets

ADAPTOR TOP

This application is a continuation application of allowed application Ser. No. 08/313,651 filed Sep. 26, 1994, now U.S. Pat. No. 5,693,027, which is a continuation of 08/053,502 filed Apr. 27, 1993, now abandoned, which is a continuation of 07/768,684 filed Oct. 9, 1991 and claims priority of application Serial No. PCT/DK91/00282 filed Sep. 20, 1991 in the PCT, and Danish application Serial Nos. 2282/90 and 0926/91 filed respectively on Sep. 21, 1990 and May 16, 1991, the contents of which are fully incorporated herein by reference in their entirety.

The invention relates to ampoules for pen syringes. Such ampoules are commonly shaped as a glas tube being at one end closed by a piston, which may be pressed into the tube to expell the content of the tube at the other end of the tube. This other end is formed as a bottle neck, the outer end of which is closed by a rubber membrane, which may be pierced by an injection needle through which the content is expelled.

In a standard cartridge the outer end of the bottleneck is provided with an external flange supporting the rubber membrane, and this membrane is sealingly secured over the opening of the neck against the flange by a metal cap having a central opening exposing the central part of the membrane over the opening of the neck, having side walls extending along the sides of the membrane and the flange, and having its end beaded to grip under the lower side of the flange.

As new types of pen syringes were developed the cartridges or at least the neck thereof was given different shapes to accomodate these types of syringes. Especially the use of plastic closures instead of the standard metal cap has made it necessary to design the flanges for cooperation with such plastic tops which demand a greater accuracy of the glas flange if a reliable sealing shall be obtained. Conseqently, the different insulin types each have to be marketed in different types of cartridges whereby the manufacturing and the stockpiling is made complicated.

It is the object of the invention to provide a system of tops making a standard cartridge usable in an optional pen.

This is obtained by a plastic top which according to the invention has a bore for receiving the neck part of the cartridge, the bore having a diameter fitting over the metal cover, the inner wall of the bore being provided with protrusions for gripping behind the edge of the metal cover when the neck part is inserted into the bore, and the outer contour of the top being formed to adapt the chosen syringe type.

By using such a plastic top only one type of cartridges has to be manufactured as the adaption to a chosen type of syringe is made by the choice of plastic top. This means that the department filling the cartridges will not have to dispose of different filling machines or to rearrange existing machines to fill different types of cartridges with the same type of medicine. The mounting of the plastic top need not take place under sterile conditions as do the filling, and as the plastic top is of no importance to the sealing of the cartridges, the high accuracy demand may be reduced as the protrusions in the bore only have to secure the plastic top so that it cannot easily be removed, but do not have to prevent rotation or small axial movements of the plastic top on the neck part.

According to the invention the plastic top may be provided with a thread coaxial with the bore to receive a threaded needle hub carrying a double pointed needle, the thread of the top being provided so that when the needle hub is screwed onto the top mounted on a cartridge the one pointed end of the needle will penetrate the rubber membrane of the cartridge. This way the plastic top may serve the same purpose as do the known plastic closures.

The plastic top may be provided with means for keyed engagement with corresponding means in a syringe to keep it unrotable when mounted with a cartridge in the syringe. This is of importance when a needle should be screwed onto the top. In some types of syringes such keyed engagement between cartridge and syringe is further used to ensure that only a certain type of cartridge is used in the syringe.

According to the invention the top may be made from a coloured plastic in accordance with a colour code system for the content of the cartridges. Such a colour code system exists for isulin preparations revealing if a cartridge contains slow or quick acting insulin or a mixture thereof. Especially where the code top having an external thread is used the user is reminded of the type of medicine in the cartridge each time he has to screw a new needle onto the thread of the plastic top.

The plastic top may surround only the neck part of the cartridge or it may cover a bigger or smaller part of the cartridge and even form a part of the housing of a syringe, which may simplify the changing of cartridges.

Figure 2:
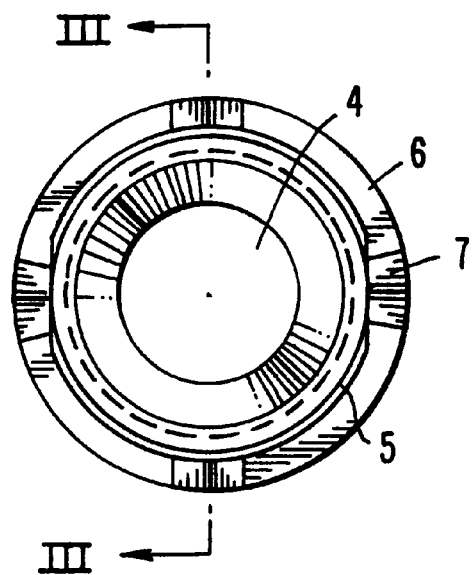
Figure 3:
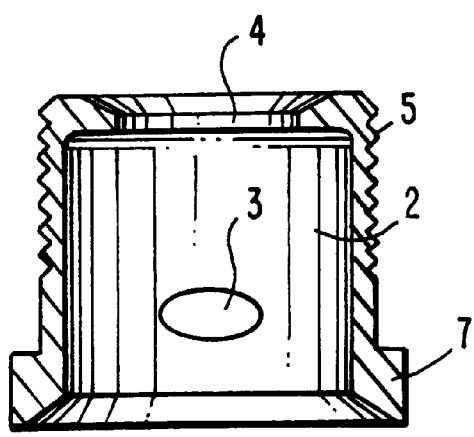
Figure 4:
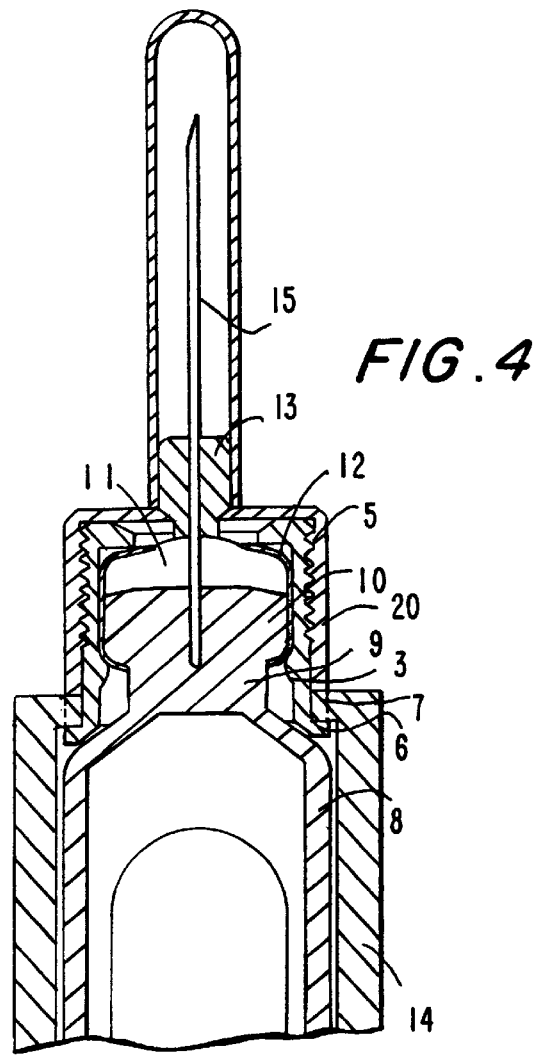
Figure 5:
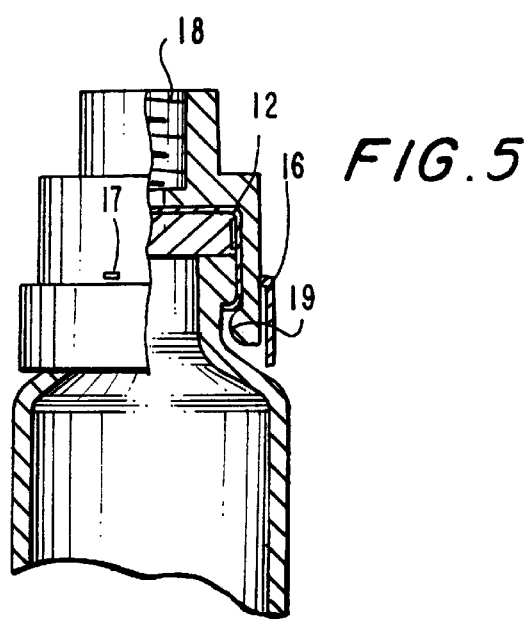

The invention will now be described in further details with reference to the drawing, wherein FIG. 1 shows a front view of an embodiment of an adaptor top according to the invention, FIG. 2 shows a plan view of the embodiment shown in FIG. 1, FIG. 3 shows a sectional view along the line III—III in FIG. 2, FIG. 4 shows a cylinder ampoule with an adaptor top as illustrated in FIGS. 1–3 mounted in a pen syringe, FIG. 5 shows another embodiment of an adaptor top according to the invention.

An adaptor top shown in FIG. 1 comprises a body 1 with a bore having a diameter slightly bigger than the diameter of the metal cap of a standard cylinder ampoule. The cylindric inner wall 2 of the bore is provided with protrusions 3 which may grip under the beaded lower edge of the metal cap of a standard ampoule, when the top is fitted with its bore over the closure of the ampoule. In the shown embodiment there are three protrusions with an angular spacing of 120°, but more protrusions or a single ring shaped protrusion may be used just as the scope of the invention is not deviated from by using two or one protrusion.

The protrusions 3 are given a heighth ensuring a good grip under the edge of the metal cap and the top is mounted by pressing the top with its bore over the metal cap making the protrusion pass the cap by the plastic material of the top being indicentally deformed. The protrusions 3 are placed in the bore of the body 1 in a position making them reach their gripping position under the edge of the metal cap before the insertion of the ampoule neck part into the bore is stopped by the top of the closure abutting the bottom of the bore or the lower edge of the body 1 abutting the ampoule around its neck.

At the bottom of its bore 2 the adaptor top is provided with an opening 4 exposing part of the top of the metal cap with the rubber membrane layed bare. The adaptor top in the shown embodiment is intended for a needle in a hub having an internal thread and consequently it is provided with an outer thread 5 for receiving such a hub with its needle projecting through the opening 4.

At its lower end the body 1 is provided with a flange 6 having triangular nobs 7 intended for cooperation with the syringe using an ampoule carrying this top. The engagement between the knobs 7 and corresponding recesses in the syringe keeps the top unrotable during screwing on the needle hub.

The outer cylindric contour of the body is shown with opposite flat cuts removing the thread 5 on opposite sides of the cylinder. Such cuts in the cylindric body shape may be made to provide a key for cooperation with a specific syringe, but is in the shown embodiment made for pure moulding related reasons.

FIG. 4 shows schematically the relevant parts of the syringe with an ampoule mounted using an adaptor top according to the invention. The parts of the adaptor top are given the reference numbers of similar parts in the embodiment shown in FIGS. 1–3. A standard ampoule 8 has a neck 9 with a flange 10 against which a rubber membrane 11 is sealingly secured by a metal cap 12 beaded under the flange 10. The bottom of the cup shaped cap 12 has an opening up through which part of the membrane 11 protrudes. The adaptor top is passed with its bore over the cap 12 and pressed down to make the protrusion 3 pass the metal cap and grip under the lower beaded edge of this cap. A neddle hub 13 has a depending tubular skirt 20 having an internal thread to be screwed onto the outer thread 5 of the adaptor top with its needle 15 piercing the membrane 11 and projecting into the opening of the neck part of the ampoule. From the drawing it is noticed that the adaptor top is not the type having three protrusions 120° displaced, but has oppositely placed protrusions 3. Similarly, the knobs 7 in FIG. 4 are not placed diametrically opposite each other as they are in FIGS. 1–3.

The ampoule 8 with the adaptor top is inserted in a syringe housing 14 from the rear end thereof with the adaptor top projecting through an end wall of the syringe housing 14 and with the flange 6 of the adaptor top abutting this end wall. The end wall has recesses to be engaged by the knobs 7 on the flange 6 and the top is this way held unrotably so that the needle hub may be screwed on the top. When screwed on the top the needle hub may be tightenen to clamp the end wall of the housing 14 between the flange 6 and the lower edge of the skirt 20. In another not shown embodiment the flange 6 may be omitted and the knobs 7 may be provided on the outer wall of the top and may be received in triangular recesses in the end wall of the syringe housing 14.

In this way the ampoule is held in the syringe in a way making it easy to take out an empty ampoule by unscrewing the needle hub 7 as the ampoule is not wedged in the housing.

FIG. 5 shows another embodiment of an adaptor top mounted on a standard ampoule. Instead of discrete protrusions a ringshaped protrusion 19 is running at the inner side of the bore. To make it possible to press this top over the metal cap 12 the lower edge carrying the protrusion has either to be very resillient or even to be slotted to enable a deformation allowing the protrusion to pass over the metal cap of the ampoule. Thereby the adaptor top may be too easy to remove unless as shown it is provided with an unresillient locking ring 16 which is kept in position by locking fingers 17. This adaptor top is shown having in its opening an inner thread 18 for receiving a needle hub having an outer thread.

What is claimed is:

1. A plastic adaptor top for mounting on a standard cartridge of the kind having a neck part with a flange and being closed by a rubber membrane sealingly secured against the flange by a metal cover having its edge beaded behind the flange, said adaptor top comprising: an axially extending bore (2) having a diameter conforming to the diameter of the metal cover of such standard cartridge and having at least one radially inwardly extending protrusion, the top being made of plastic material which may be deformed to allow the said at least one protrusion to be pressed radially outwardly when the neck part of a cartridge is pressed into the bore (2), to pass over the metal cover of such standard cartridge, and wherein said at least one protrusion is positioned axially within said bore so as to grip behind the beaded edge of such metal cover, after such metal cover is pressed into said bore to secure said adaptor top to the metal cover, and wherein said adaptor top has an outer contour suitable to be received in and engage an interior portion of a syringe for positioning such standard cartridge therewithin, said adaptor top thereby being suitable to make a standard cartridge usable in a syringe which it otherwise would not fit.

2. The adaptor top according to claim 1, further comprising a thread (5, 18) coaxial with the bore (2) which thread is provided as an outer thread on the outer contour of the plastic top.

3. A plastic adaptor top for mounting on a standard cartridge of the kind having a neck part with a flange and being closed by a rubber membrane sealingly secured against the flange by a metal cover having its edge beaded behind the flange, said adaptor top comprising: an axially extending bore (2) having a diameter conforming to the diameter of the metal cover of such standard cartridge, wherein said adaptor top has an outer contour suitable to be received in and engage an interior portion of a syringe for positioning such standard cartridge therewithin, said adaptor top thereby being suitable to make a standard cartridge usable in a syringe which it otherwise would not fit, wherein said outer contour comprises interlocking means for interlocking engagement with corresponding means in a syringe to prevent rotation of said adaptor top when said adaptor top is inserted into such a syringe and wherein said adaptor top further comprises a thread coaxial with the bore to receive a threaded needle hub.

4. The adaptor top according to claim 3, wherein said interlocking means are knobs (7) at the lower end of the top, said knobs (7) having triangular cross-sections with an apex directed upwardly.

5. The adaptor top in accordance with claim 1 for use with a standard insulin cartridge which may contain one of various types of insulin, wherein said adaptor top is colored in accordance with a color code system in which each color indicates a particular type of insulin such that said adaptor top, when mounted on a standard insulin cartridge indicates the type of insulin contained in such cartridge.

* * * * *